(12) United States Patent
Cheong et al.

(10) Patent No.: US 7,432,080 B2
(45) Date of Patent: Oct. 7, 2008

(54) PROCESS FOR THE PRODUCTION OF TEICOPLANIN

(75) Inventors: Soo-Ryun Cheong, Seoul (KR); Sang-Young Kim, Gwangmyeong-Shi (KR); Youn-Woo Lee, Seoul (KR); Jung-Kul Lee, Seoul (KR); Hyeon-Cheol Lee, Seoul (KR); Hyung-Moo Jung, Seoul (KR); Bong-Seoung Koo, Seoul (KR)

(73) Assignee: Biongene Co., Ltd., Seoul (KR)

( * ) Notice: Subject to any disclaimer, the term of this patent is extended or adjusted under 35 U.S.C. 154(b) by 333 days.

(21) Appl. No.: 11/013,736

(22) Filed: Dec. 17, 2004

(65) Prior Publication Data

US 2006/0134757 A1    Jun. 22, 2006

(51) Int. Cl.
*C12P 21/04* (2006.01)
*C12P 21/00* (2006.01)

(52) U.S. Cl. .................. 435/71.3; 435/252.1

(58) Field of Classification Search ............. None
See application file for complete search history.

(56) References Cited

U.S. PATENT DOCUMENTS 4,239,751 A * 12/1980 Coronelli et al. ............ 424/118

FOREIGN PATENT DOCUMENTS

| KR | 2002057853 | * | 7/2002 |
| KR | 373510 | * | 2/2003 |
| KR | 2004076836 | * | 9/2004 |

* cited by examiner

*Primary Examiner*—Irene Marx
(74) *Attorney, Agent, or Firm*—Kenyon & Kenyon LLP

(57) ABSTRACT

The present invention provides a newly isolated mutant culture of *Actinoplanes teichomyceticus* BNG 2315. This culture is capable of producing teicoplanin more than 60 times productivity than those reported before (e.g., *Actinoplanes teichomyceticus* nov. sp. ATCC 31121). The present invention also provides a fermentation process for the production of teicoplanin in an aerobic condition using the mutant strain *Actinoplanes teichomyceticus* BNG 2315 in a culture-medium comprising carbon sources, nitrogen sources and mineral salts.

1 Claim, 3 Drawing Sheets

PROCESS FOR THE PRODUCTION OF TEICOPLANIN

BACKGROUND OF THE INVENTION

The present invention relates to a microorganism producing teicoplanin and a fermentation process for preparing teicoplanin in an aerobic condition, using an isolated mutant strain belonged to *Actinoplanes teichomyceticus* species on the culture medium containing assimilable carbon, nitrogen sources and mineral salts.

In particular, the present invention concerns to an isolated mutant strain *Actinoplanes teichomyceticus* BNG 2315 (KCCM-10601) producing teicoplanin more than about sixty times productivity than those of described in the prior arts (U.S. Pat. No. 4,239,751) as well as a fermentation process for preparing teicoplanin in an aerobic condition using the said mutant strain.

Teicoplanin, one of antibiotics produced by *Actinoplanes teichomyceticus*, has been classified from the vancomycin-ristocetin family of glycopeptide antibiotics. Its mechanism is to inhibit the cell wall biosynthesis and it has been administered against gram-positive antibiotics-resistant pathogens, such as, methicillin-resistant *Staphylococcus aureus*, coagulase-negative *Staphylococci, Clostridia,* and *Enterococci.*

The emergence of microorganisms resistant to various kinds of antibiotics, especially, methicillin-resistant microorganisms caused by administration of too much antibiotics may result in severe health problem. Further, the methicillin-resistant microorganism is also resistant against any other antibiotics, such as, aminoglycosides, tetracyclines, cephalosporins, cephamycins, penems, carbapenems, and macrolides, which causes the severe disease.

World-wide problem of the protection from methicillin-resistant *S. aureus* have resulted in the increased use of vancomycin and teicoplanin, those are, the only agents for effective treatment of these pathogens.

Teicoplanin is an antibiotic produced by cultivating the strain *Actinoplanes teichomyceticus* nov. sp. (ATCC-31121) in a culture medium containing the carbon source, nitrogen source and inorganic salts (J. Antibiotics, 276-283, 1978; U.S. Pat. No. 4,239,751). However, the strain described in the U.S. Pat. No. 4,239,751 is undesirable in a commercialized scale, because it produces teicoplanin less than 50 mg/L productivity in a high cost.

Thus, the isolation of mutant strain having higher productivity in comparison to those producing teicoplanin has been required, as well as the development of fermentation process for preparing teicoplanin in an aerobic condition using said mutant strain.

Surprisingly, in the course of our screening research for teicoplanin-producing strains of *Actinomycetales* of the family *Actinoplanaceae,* we have isolated a novel strain from a soil sample collected at Sorak Mountain, Korea. Said isolated strain produces teicoplanin about 20 times productivity than those of described in prior art (U.S. Pat. No. 4,239,751).

This strain has been subjected under repeated mutagenic treatment. Then, teicoplanin-resistant mutants were isolated. The mutant strain produces teicoplanin about 60 times productivity than those described in the U.S. Pat. No. 4,239,751.

SUMMARY OF THE INVENTION

The object of the present invention is to provide a fermentation method for maximum production of teicoplanin using a mutant of *Actinoplanes teichomyceticus* BNG 2315 deposited to Korean Culture Center of Microorganism with accession number KCCM-10601 comprising the steps of: i) fermenting mutant cells on production medium comprising glucose 15~25 g/L, dextrin 40~80 g/L, peptone 4~6 g/L, rapeseed meal 16~20 g/L, soybean flour 16~20 g/L, $MgSO_4 \cdot 7H_2O$ 0.4~0.6 g/L, $CaCO_3$ 4~6 g/L, and NaCl 1.0~1.4 g/L on condition that aeration rate of the medium is 0.5~2.0 volume of air per volume of medium per minute, ii) removing the mutant cells and other residue from the fermentation medium; and iii) separating and recovering teicoplanin from the fermentation medium of step (ii).

Further, said mutant cells used for fermentation are prepare by cultivating *Actinoplanes teichomyceticus* BNG 2315 (KCCM-10601) in the medium comprising glucose 25~35 g/L, yeast extract 2.0~3.0 g/L, soybean flour 7.0~11.0 g/L, rapeseed meal 7.0~11.0 g/L, NaCl 1.0~1.4 g/L, $CaCl_2$ 0.08~0.12 g/L, $MgSO_4 \cdot 7H_2O$ 0.4~0.6 g/L and $CaCO_3$ 4~6 g/L.

On the other hand, the present invention also provides an isolated *Actinoplanes teichomyceticus* BNG 2315 deposited to Korean Culture Center of Microorganism with accession number KCCM-10601.

DETAILED DESCRIPTION OF THE INVENTION

Figure 1:
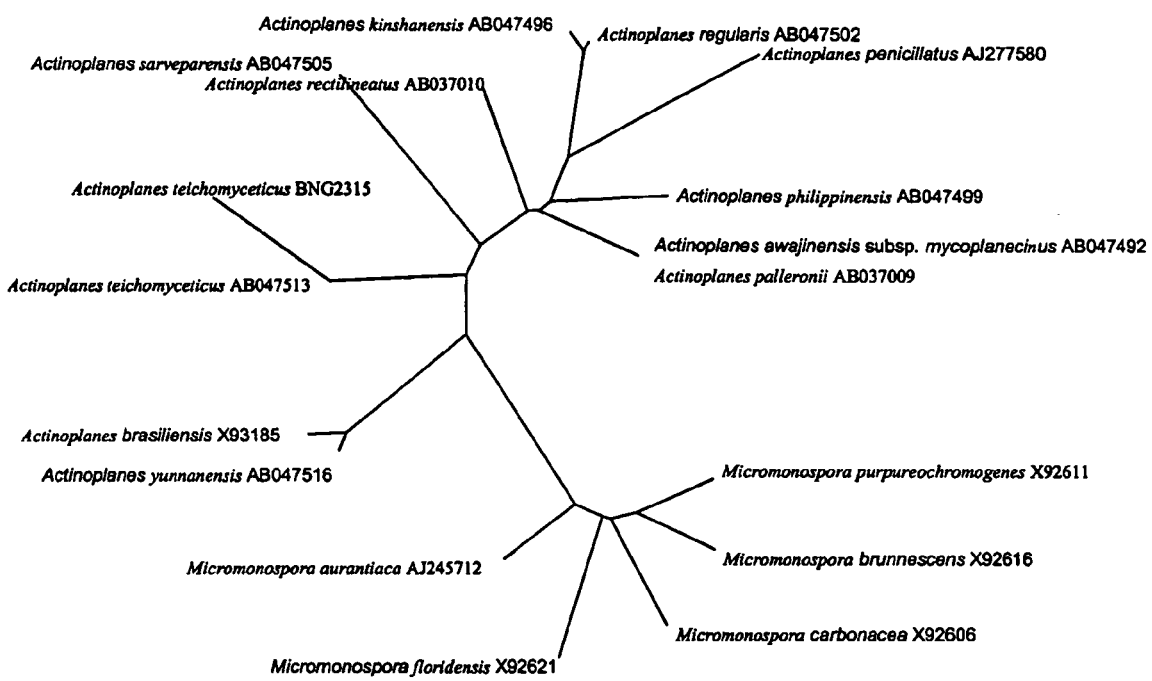
FIG. 1 shows phylogenetic tree in which *Actinoplanes teichomyceticus* BNG 2315 is positioned by comparative 16s rDNA sequencing.

Said mutant strain has been determined as belonging to *Actinoplanes teichomyceticus* through taxological investigations, such as, the cellular fatty acid analysis and 16s rDNA sequence analysis.

However, the mutant strain is clearly distinguished from the original strain described in U.S. Pat. No. 4,239,751 in the point of some cultural and physiological characteristics as well as the capability producing teicoplanin. Thus, the newly isolated culture has been named as *Actinoplanes teichomyceticus* BNG 23, and its mutant strain obtained by UV radiation treatment to said culture has been named as *Actinoplanes teichomyceticus* BNG 2315.

Then, the mutant strain has been deposited as *Actinoplanes teichomyceticus* BNG 2315 in the Korea Culture Center of Microorganism located at 361-221, Yurim building, Hongje 1-Dong, Seodaemun-Gu, Seoul, Korea on Jul. 28, 2004 with the accession number KCCM-10601 under the Budapest Treaty.

EXAMPLE I

Isolation of Microorganism Producing Teicoplanin

The mutant strain *Actinoplanes teichomyceticus* BNG 23 was isolated from a soil sample collected at Sorak Mountain, Korea by the capillary tube method. Microorganisms from a soil sample described above were inoculated on selection medium for identification of members of *Actinomycetales*. Candidated cultures selected as members of the *Actinomycetales* by the taxonomical properties were then planted in aqueous nutrient medium containing glucose, dextrin, soybean flour, potato protein, and mineral salts. The culture broths were filtered and analyzed by High Performance Liquid Chromatography (HPLC) using standard protocol for the assay of teicoplanin. The candidated cultures selected as teicoplanin producer were subjected to the microbial assay performed on Difco Nobel agar medium inoculated with 0.3% (v/v) of an aqueous suspension of *S. aureus* which contained $10^6$ cells per 1 ml. Finally, candidated cultures selected as teicoplanin producer were taxonomically identified and the compounds assumed as teicoplanin produced by the cultures were analyzed for its physicochemical properties.

In conclusion, this inventors have isolated a novel culture that belongs to *Actionplanes teichomyceticus* and produces teicoplanin about 20 times productivity than those described in the prior art (U.S. Pat. No. 4,239,751).

EXAMPLE II

Isolation of Hyper-Producing Mutant for Teicoplanin

In order to isolate mutant strains producing teicoplanin more efficiently than mother strain described above, treatment for mutagenesis was performed by UV radiation. Mother strain was cultivated on oatmeal agar slant at 32° C. for 12 days. Normal saline buffer was added into the slant and mixed them vigorously, and then the suspension was filtered with No. 2 Wattman Paper. The spore suspension was subjected to UV radiation by 30 W UV lamp and stood still at 4° C. for 2 hours in the dark. The spore suspension was transferred on soytone agar medium containing 100 mg/L teicoplanin and incubated at 32° C. for 7 days.

The culture of pathogenic microorganism of *Bacillus subtilis* was inoculated on the colonies grown on the plate and it was incubated at 32° C. for 18 hours. Colonies that make larger inhibition zone around themselves than that formed around the mother strain were selected as candidated mutants and they were named *Actionplanes teichomyceticus* BNG with the number according to the colonies. The candidated mutants were cultivated in 7 L batch fermenter containing the production medium listed in table 1 below for 120 hours.

The mutants selected in fermenter scale were measured for their productivities and stabilities through 5 separated experiments. Surprisingly, this inventors have isolated the mutant strain *Actinoplanes teichomyceticus* BNG 2315 producing teicoplanin about 60 times productivity than those reported in the prior art (U.S. Pat. No. 4,239,751) and have deposited it in the Korea Culture Center of Microorganism as the accession number KCCM-10601 under the Budapest Treaty.

TABLE 1

| Composition of Production Medium | |
|---|---|
| Medium | Composition (%) |
| Agar plate | Oatmeal 1.5%, Starch 1.0%, Agar 2.0% |
| Agar slant | Oatmeal 1.5%, Starch 1.0%, Agar 2.0% |
| Seed culture | Yeast extract 0.5%, Malt extract 1.0%, Bacto Peptone 0.5% |
| Production culture | Soybean flour 1.8%, Rapesed meal 1.8%, Dextrin 6%, Glucose 2.0%, $MgSO_4 \cdot 7H_2O$ 0.05%, $CaCO_3$ 0.5% |

EXAMPLE III

Taxonomical Identification of the Mutant Strain *Actinoplanes teichomyceticus* BNG 2315

The newly isolated strain producing teicoplanin was taxonomically identified by the analysis of cellular fatty acid, cell wall composition, and 16s rDNA sequence. The analysis of cellular fatty acid shows 98% of similarity with *Actinoplanes teichomyceticus* and the diaminopimeric acid of the strain is meso-form like that of *Actinoplanes teichomyceticus*. In particular, the sequence of 16s rDNA of the newly isolated strain producing teicoplanin shows 99% homology with that of *Actinoplanes teichomyceticus*. As a result, this newly isolated strain producing teicoplanin was determined as belonged to *Actinoplanes teichomyceticus*. However, this strain is clearly distinguished from the strain *Actinoplanes teichomyceticus* described in U.S. Pat. No. 4,239,751 by several cultural and physiological characteristics described below. Thus, the mutant strain has been assigned as *Actinoplanes teichomyceticus* BNG 2315 and deposited in the Korea Culture Center of Microorganism as the accession number KCCM-10601 under the Budapest Treaty.

FIG. 1 shows the detailed phylo-genetic tree in which *Actinoplanes teichomyceticus* BNG 2315 is positioned by comparative 16s rDNA sequencing.

EXAMPLE IV

Cultural Characteristics of the Mutant Strain *Actinoplanes teichomyceticus* BNG 2315

(1) Macroscopic Examination

The sizes of colonies produced on oatmeal agar medium are 3~4 mm in diameter. The shape of colonies is well-defined and regular contours and central dome-like protuberance with a pale orange color. A light orange to deep orange vegetative mycelium is produced on most of media. However, the color of the vegetative mycelium is light brown on potato, skim milk and avena-yeast agars medium. In some medium, a light brown soluble pigment is produced. A well-developed powdery aerial mycelium made up of long hyphae is found on some medium.

Table 2 reports the cultural characteristics of *Actinoplanes teichomyceticus* BNG 2315 cultivated on various standard media. The cultural characteristics were determined after 7~14 days of incubation at 30° C.

TABLE 2

Cultural characteristics (incubated at 32° C. for 14 days)

| Medium | Aerial mycelia | | | Sporangia | | Soluble pigment |
|---|---|---|---|---|---|---|
| | Growth | Formation | Color | Formation | Color | |
| Medium ISP No. 2 | Abundant | Abundant | Pale orange | Abundant | Light pink | Amber |
| Medium ISP No. 3 | Abundant | Abundant | Pale orange | Abundant | Light pink | None |
| Medium ISP No. 4 | Abundant | Abundant | deep orange | Scarce | Pale pink | None |
| Medium ISP No. 5 | Abundant | Abundant | Pale orange | Moderate | Light pink | Metal pink |
| Medium ISP No. 6 | Poor | Scarce | Pale crane | None | | Black brown |
| Medium ISP No. 7 | Moderate | Moderate | White | Scarce | Pale orange | Pinkish brown |
| Starch agar | Poor | Scarce | Orange-red | Scarce | Light pink | None |
| Skim milk agar | Abundant | Abundant | Light brown | None | | Amber |
| Potato agar | Abundant | Abundant | Light brown | Abundant | Light pink | Amber |
| Clacium-malate agar | Poor | Moderate | Pale orange | Moderate | Pale pink | Cheese yellow |
| Glucose-asparagine agar | Abundant | Abundant | orange | Abundant | Deep orange | Rose yellow |
| Avena-Yeast agar | Abundant | Abundant | Light brown | Moderate | White | Yellow-brown |

(2) Microscopic Examination

Sporangia, abundantly produced on most of media, are mainly found on the dome of the colony. The sporangia are spherical to oval, with regular contours and have diameters ranging from 15~20 μm. Sporangiophors are straight, about 15 μm and 2 μm in diameter. The highly motile spores are spherical to oval, with diameters of 1.5~2 μm. The vegetative mycelium is composed of thin, twisted and branched hyphae 0.5~1 μm in diameter.

EXAMPLE V

Physiological Characteristics of the Mutant Strain *Actinoplanes teichomyceticus* BNG 2315

Physiological characteristics of the mutant strain *Actinoplanes teichomyceticus* BNG 2315 compared to other teicoplanin producers. Table 3 reports the utilization of carbon sources.

Table 4 reports other physiological characteristics. The strain *Actinoplanes teichomyceticus* BNG 2315 has been cultured concomitantly with: *A. uthaensis, A. coloradoensis*, and *A. teichomyceticus*. Compared with general characteristics of *Actinoplanes teichomyceticus* species, the characteristics of *Actinoplanes teichomyceticus* BNG 2315 for the utilization of carbohydrates was identical except utilization of rhamnose and lactose. In addition, the main physiological characteristics were also identical except gelatin liquefaction and Calcium-malate hydrolysis. As a result, this mutant strain was determined as belonging to *Actinoplanes teichomyceticus* but was assigned as *Actinoplanes teichomyceticus* BNG 2315 because it could be clearly distinguished from all these species on the basis of physiological characteristics as well as of morphological and pigmentation characteristics. It has been deposited in the Korea Culture Center of Microorganism with an accession number KCCM-10601 under the Budapest Treaty on Jul. 28, 2004.

TABLE 3

Utilization of carbohydrates

| | Actinoplanes utahhensis | Actinoplanes coloradoensis | Actinoplanes teichomyceticus | Actinoplanes teichomyceticus BNG2315 |
|---|---|---|---|---|
| Arabinose | + | + | + | + |
| Xylose | + | + | + | + |
| Glucose | + | + | + | + |
| Fructose | + | + | + | + |
| Mannose | + | + | + | + |
| Sucrose | + | + | + | + |
| Starch | + | − | + | + |
| Mannitol | + | + | + | + |
| Innositol | − | − | − | − |
| Rhamnose | + | + | − | + |
| Raffinose | − | − | − | − |
| Lactose | + | + | + | ± |

TABLE 4

Physiological characteristics

| | Actinoplanes Utahhensis | Actinoplanes Coloradoensis | Actinoplanes Teichomyceticus | Actinoplanes teichomyceticus BNG2315 |
|---|---|---|---|---|
| Starch hydrolysis | + | + | + | + |
| Milk peptonization | + | − | + | ± |
| Gelatin liquefaction | ± | − | + | − |
| Casein hydrolysis | + | + | + | + |
| $H_2S$ formation | + | + | + | + |
| Melanin production | + | + | + | + |
| Tysosine reaction | + | + | − | − |
| Nitrate reduction | + | + | + | + |
| Milk coalgulation | − | − | − | − |
| Cellulose decomposition | − | − | − | − |
| Ca-malate hydrolysis | | | − | + |
| Growth pH | 3.5~9.0 | 4.0~8.5 | 3.5~8.5 | 5.0~8.5 |
| Growth temperature | 15~42 | 4.0~42 | 15~30 | 15~37 |
| Optimum growth temperature | 20~37 | 15~37 | 28~37 | 28~34 |
| Cell wall type | meso-DAP | meso-DAP | meso-DAP | meso-DAP |

EXAMPLE VI

Production of Teicoplanin by Aerobic Fermentation

For the production of teicoplanin, the mutant strain *Actinoplanes teichomycemyceticus* BNG 2315 is fermented under aerobic conditions in an aqueous nutrient medium containing assimilable sources of carbon, nitrogen and inorganic salts. More specifically, *Actinoplanes teichomycemyceticus* BNG 2315 is aerobically pre-cultured in a nutrient medium until substantial mycelial growth is present, at a pH value ranging 5~9, more preferably at pH 7. The flasks are shaken for 24~48 hours at 28~34° C., more preferably at 32° C., and then the pre-cultures are used to inoculate jar fermenters at the final concentration of 5~10%. As an example of the nutrient medium, a pre-culture may have the following composition (g/L) as shown in table 5.

TABLE 5

Composition of the pre-culture medium

| Components | Concentration (g/L) |
|---|---|
| Glucose | 20 |
| Yeast extract | 4 |
| Peptone | 4 |
| $KH_2PO_4$ | 2 |
| $K_2HPO_4$ | 4 |
| $MgSO_4 \cdot 7H_2O$ | 0.5 |

The fermentation of *Actinoplanes teichomyceticus* BNG 2315 is carried out as follows. In small scale fermentation, the pre-cultures of *Actinoplanes teichomyceticus* BNG 2315 is inoculated to 7 L jar fermenters containing the production medium listed in Table 6.

TABLE 6

Composition of the Seed-culture medium

| Components | Concentration (g/L) |
|---|---|
| Glucose | 30 |
| Yeast extract | 2.5 |
| Soybean flour | 9 |
| Rapeseed meal | 9 |
| NaCl | 1.2 |
| $CaCl_2$ | 0.1 |
| $MgSO_4 \cdot 7H_2O$ | 0.5 |
| $CaCO_3$ | 5 |

The inoculum ranges 3~15%, more preferably is 5%. The fermentation batches are incubated under aerobic conditions with agitation at 900 rpm and with aeration maintained above 30% of air-saturation. The temperature is maintained at 25° C.~37° C., more preferably at 32° C., and pH is not controlled although it alters during fermentation.

In large scale fermentation (5,000 L), the pre-cultures of *Actinoplanes teichomyceticus* BNG2315 is inoculated to the seed-fermenters (500 L) containing 300 L of sterilized medium listed in Table 6, and then incubated at 30° C. for 48 hours under the aerobic conditions said above.

The seed-culture (300 L) is inoculated to the main fermenters (5,000 L) containing 3,000 L of the production medium listed in Table 7.

TABLE 7

Composition of the production medium

| Components | Concentration (g/L) |
|---|---|
| Glucose | 20 |
| Dextrin | 60 |
| Yeast extract | 5 |
| Soybean flour | 18 |
| Rapeseed meal | 18 |

TABLE 7-continued

Composition of the production medium

| Components | Concentration (g/L) |
|---|---|
| NaCl | 1.2 |
| $CaCl_2$ | 0.1 |
| $MgSO_4 \cdot 7H_2O$ | 0.5 |
| $CaCO_3$ | 5 |

The main fermentation is carried out under submerged aerobic condition with agitation (80~150 rpm) and aeration (50~200(v/v) %, more preferably 150(v/v) % volume of medium).

At intervals, culture broth is taken and analyzed for growth, the consumption of sugars, and the concentration of teicoplanin. 10 ml of culture broth is adjusted to pH 11 with 5N NaOH and centrifuged at 450 g for 10 minutes. Growth is measured as PMV (Packed Mycelial Volume) and the concentration of teicoplanin is determined by HPLC (High Performance Liquid Chromatography) comprising C18 reversed phased column, UV detector, and quaternary pump. The amount of total sugar is determined by phenol-sulfuric method and the concentration of glucose is measured by DNS method.

Figure 2:
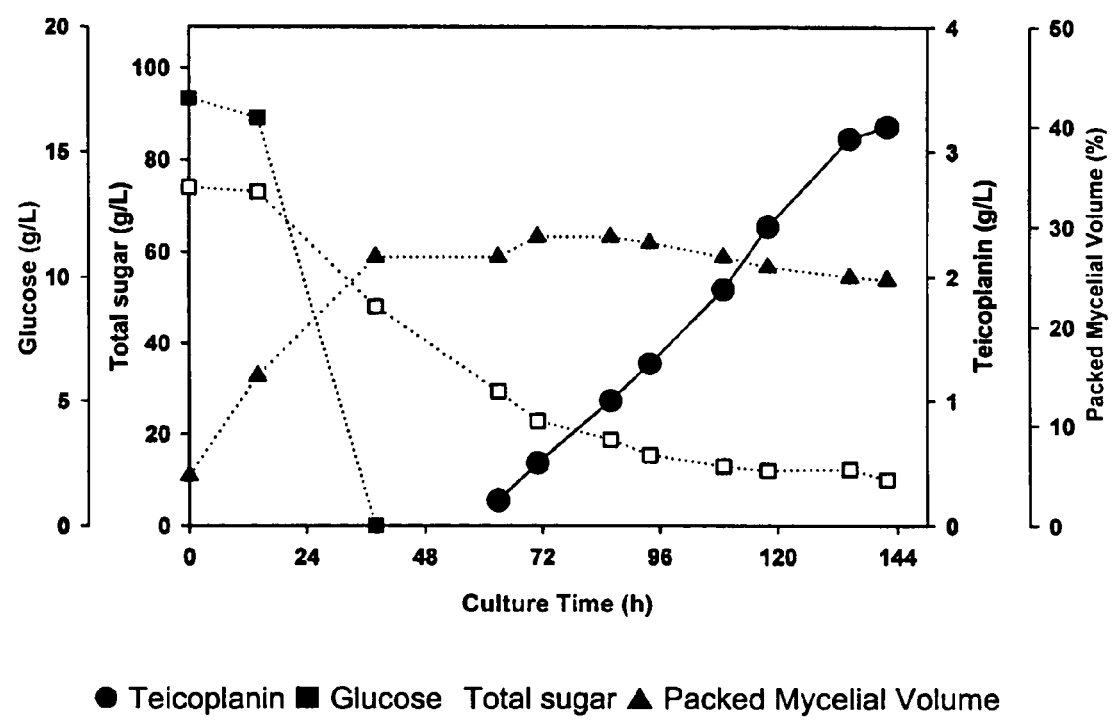
FIG. 2 shows time-course of the fermentation using the mutant strain *Actinoplanes teichomyceticus* BNG 2315 in 5,000 L scale.

The time-course of the fermentation in 5,000 L scale is shown in FIG. 2. The synthesis of teicoplanin starts when the growth phase has ended and when the residual total sugar is less than 30 g/L. The consumption of glucose is completed in 36 hours during the logarithmic growth phase and then dextrin is consumed for growth and the synthesis of teicoplanin.

The pH of the medium decreased during the growth phase to pH 6.5 then rose up to pH 8.0 during the antibiotic production phase (data not shown in FIG. 2). The growth reaches 29% as PMV in 48 hours and the synthesis of teicoplanin continues more or less linearly until 140 hours, when it begins to level off. The maximal concentration of teicoplanin produced by the mutant strain *Actinoplanes teichomyceticus* BNG 2315 is 3.2 g/L, which is 64 fold more than by *Actinoplanes teichomyceticus* nov. sp. ATCC-31121 reported in the U.S. Pat. No. 4,239,751.

TABLE 8

Comparison of the productivity for teicoplanin

| Strains | Productivity |
|---|---|
| *Actinoplanes teichomyceticus* ATCC 31121 | 0.05 g/L |
| *Actinoplanes teichomyceticus* BNG 2315 | 3.0 g/L |

In the small scale fermentation (7 L), the mutant strain *Actinoplanes teichomyceticus* BNG 2315 produced teicoplanin more than 3.0 g/L within 6 days, compared to 50 mg/L by *Actinoplanes teichomyceticus* nov. sp. ATCC-31121 reported in the U.S. Pat. No. 4,239,751 as shown in Table 8. In the large scale fermentation (5,000 L), the present mutant strain *Actinoplanes teichomyceticus* BNG 2315 produced teicoplanin from 2.5 to 3.2 g/L reproducibly in several separated experiments.

Figure 3:
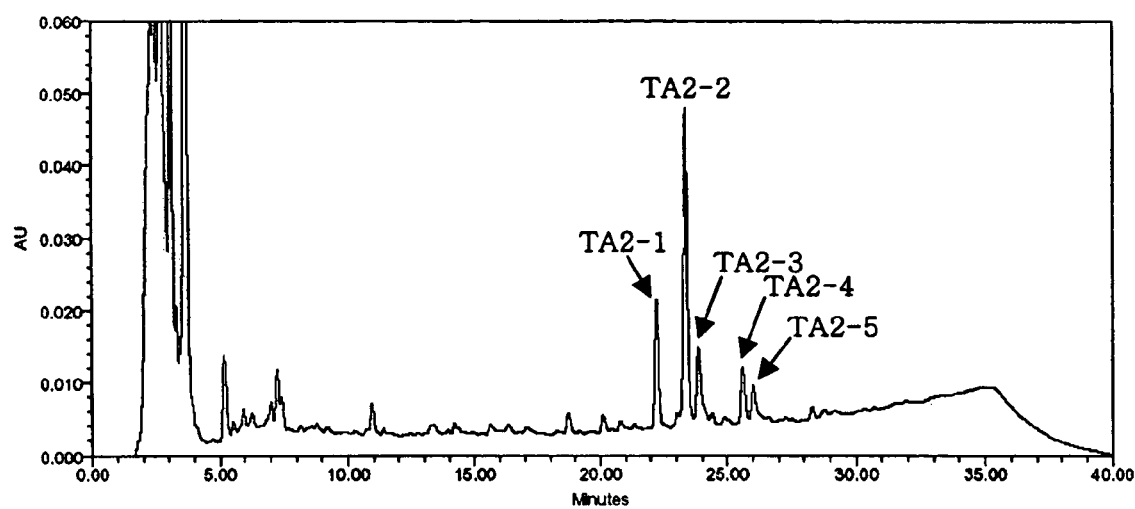
FIG. 3 shows the chromatogram of HPLC analysis of the culture broth of the mutant strain *Actinoplanes teichomyceticus* BNG 2315 (KCCM-10601).

Teicoplanin consists of a mixture of five major components designated A2-1, A2-2, A2-3, A2-4, A2-5. All teicoplanin components are glycopeptide analogs with molecular weights ranging from 1564 to 1908. They have the same core glycopeptide formed by a linear hepta-peptide aglycone and by D-mannose and D-glucosamine. The five components of the A2-group contain an additional N-acyl-glucosamine and are differentiated by different acyl-aliphatic side chains. The A2-group components may be ranked in order of increasing lipophilicity from A2-1 to A2-5 according to the retention time on reverse-phase HPLC (FIG. 3). Table 9 shows the composition of the teicoplanin A2 complex.

TABLE 9

Composition of the teicoplanin A2 complex

| Strains | Percentage composition | | | | |
|---|---|---|---|---|---|
| | A2-1 | A2-2 | A2-3 | A2-4 | A2-5 |
| ATCC-31121 | 6.4 | 59.8 | 7.9 | 12.8 | 13.1 |
| KCCM-10601 | 5.4 | 51.3 | 15.5 | 18.6 | 9.2 |

The single components of A2-group have different biological activities. A2-3 and A2-4 have twice higher biological activities than that of both A2-1 and A2-2, respectively, against *Staphylococcus aureus*.

As shown in FIG. 2 and Table 9, teicoplanin A2 complex produced by the mutant strarin *Actinoplanes teichomyceticus* BNG 2315 (KCCM-10601) also comprises five components but the composition of the A2-group is different from that produced by *Actinoplanes teichomyceticus* nov. sp. ATCC-31121 reported in the U.S. Pat. No. 4,239,751. In other words, the contents of A2-3 and A2-4 in teicoplanin A2 complex produced by the mutant strain *Actinoplanes teichomyceticus* BNG 2315 (KCCM-10601) are 2 and 1.4 fold more than those by *Actinoplanes teichomyceticus* nov. sp. ATCC-31121 reported in the U.S. Pat. No. 4,239,751, which results in the increase of the biological activity of teicoplanin complex.

In conclusion, the result of fermentations as well as cultural and physiological properties represents that the present mutant strain is clearly distinguished from other teicoplanin producers reported in prior arts.

What is claimed is:

1. A fermentation method for maximum production of teicoplanin using *Actinoplanes teichomyceticus* BNG 2315 deposited to Korean Culture Center of Microorganism with accession number KCCM-10601 comprising the steps of:

i) fermenting cells of *Actinoplanes teichomyceticus* BNG 2315 on production medium comprising glucose 15-25g/L, dextrin 40-80g/L, peptone 4-6g/L, rapeseed meal 16-20g/L, soybean flour 16-20g/L, $MgSO_4.7H_2O$ 0.4-0.6g/L, $CaCO_3$ 4-6g/L, and NaCl 1.0-1.4g/L on condition that aeration rate of the medium is 0.5-2.0 volume of air per volume of medium per minute;

ii) removing the cells and other residue from the fermentation medium; and iii) separating and recovering teicoplanin from the fermentation medium of step (ii), wherein the cells of *Actinoplanes teichomyceticus* BNG 2315 used for fermentation are pre-cultured in the seed-culture medium comprising glucose 25-35g/L, yeast extract 2.0-3.0g/L, soybean flour 7.0-11.0g/L, rapeseed meal 7.0-11.0g/L, NaCl 1.0-1.4g/L, $CaCl_2$ 0.08-0.12g/L, $MgSO_4.7H_2O$ 0.4-0.6g/L, and $CaCO_3$ 4-6g/L.

* * * * *